United States Patent
Johansson et al.

(10) Patent No.: US 12,157,006 B2
(45) Date of Patent: Dec. 3, 2024

(54) IMPLANTABLE HEARING AID SYSTEM COMPRISING A WIRELESS TRANSCUTANEOUS LINK

(71) Applicant: Oticon Medical A/S, Smørum (DK)

(72) Inventors: Martin Johansson, Askim (SE); Wilhelm Råbergh, Askim (SE); Maja Thorning-Schmidt, Smørum (DK); Martin Gylstorff, Smørum (DK); Stefan Vucurevic, Smørum (DK)

(73) Assignee: Oticon Medical A/S, Smørum (DK)

( * ) Notice: Subject to any disclaimer, the term of this patent is extended or adjusted under 35 U.S.C. 154(b) by 738 days.

(21) Appl. No.: 17/186,123

(22) Filed: Feb. 26, 2021

(65) Prior Publication Data

US 2021/0268281 A1    Sep. 2, 2021

(30) Foreign Application Priority Data

Feb. 28, 2020    (EP) .................................. 20160040

(51) Int. Cl.
| | | |
|---|---|---|
| *A61N 1/36* | (2006.01) | |
| *A61N 1/378* | (2006.01) | |
| *H04R 25/00* | (2006.01) | |

(52) U.S. Cl.
CPC ....... *A61N 1/36038* (2017.08); *A61N 1/3787* (2013.01); *H04R 25/554* (2013.01); *H04R 25/607* (2019.05); *H04R 2225/025* (2013.01)

(58) Field of Classification Search
None
See application file for complete search history.

(56) References Cited

U.S. PATENT DOCUMENTS

| | | |
|---|---|---|
| 7,599,508 B1 | 10/2009 | Lynch et al. |
| 2008/0304686 A1* | 12/2008 | Meskens ............... H04R 25/60 381/330 |

(Continued)

FOREIGN PATENT DOCUMENTS

| | | |
|---|---|---|
| EP | 3 103 511 A1 | 12/2016 |
| EP | 3 441 111 A1 | 2/2019 |
| WO | WO 2018/174728 A1 | 9/2018 |

*Primary Examiner* — Sana Sahand
(74) *Attorney, Agent, or Firm* — Birch, Stewart, Kolasch & Birch, LLP

(57) ABSTRACT

According to an embodiment, an implantable hearing aid system is disclosed. The implantable hearing aid system includes an external unit which includes an electronic unit operationally coupled to a first inductive coil arrangement configured to transmit power and/or data signals, and where the first inductive coil arrangement includes a loop structure with coils wound around and along at least a part of length of the loop structure, and the loop structure comprises an opening. Furthermore, the implantable hearing aid system includes an implantable unit which comprises a second inductive coil arrangement configured to form a transcutaneous link with the loop structure and to receive the power and/or data signals over the transcutaneous link, and where the second inductive coil arrangement is configured to be implanted fully or partially within a part of an ear of a user of the implantable hearing aid system. The external unit includes a housing and an earhook, and where a first end-face of the loop structure is arranged within the earhook and a second end-face of the loop structure is arranged within the housing or within the earhook.

20 Claims, 17 Drawing Sheets

(56) References Cited

U.S. PATENT DOCUMENTS

| | | | |
|---|---|---|---|
| 2009/0254182 A1* | 10/2009 | Kovarik | A61L 27/12 |
| | | | 623/17.11 |
| 2011/0116669 A1* | 5/2011 | Karunasiri | H04R 25/554 |
| | | | 381/330 |
| 2014/0025138 A1* | 1/2014 | Meskens | H04R 25/606 |
| | | | 607/57 |
| 2014/0050343 A1* | 2/2014 | Bjorstrup | H04R 25/02 |
| | | | 381/330 |
| 2016/0366525 A1* | 12/2016 | Bodvarsson | A61N 1/36036 |
| 2017/0050023 A1* | 2/2017 | Hillbratt | A61N 1/36038 |
| 2019/0051988 A1* | 2/2019 | Bern | H01Q 7/06 |

* cited by examiner

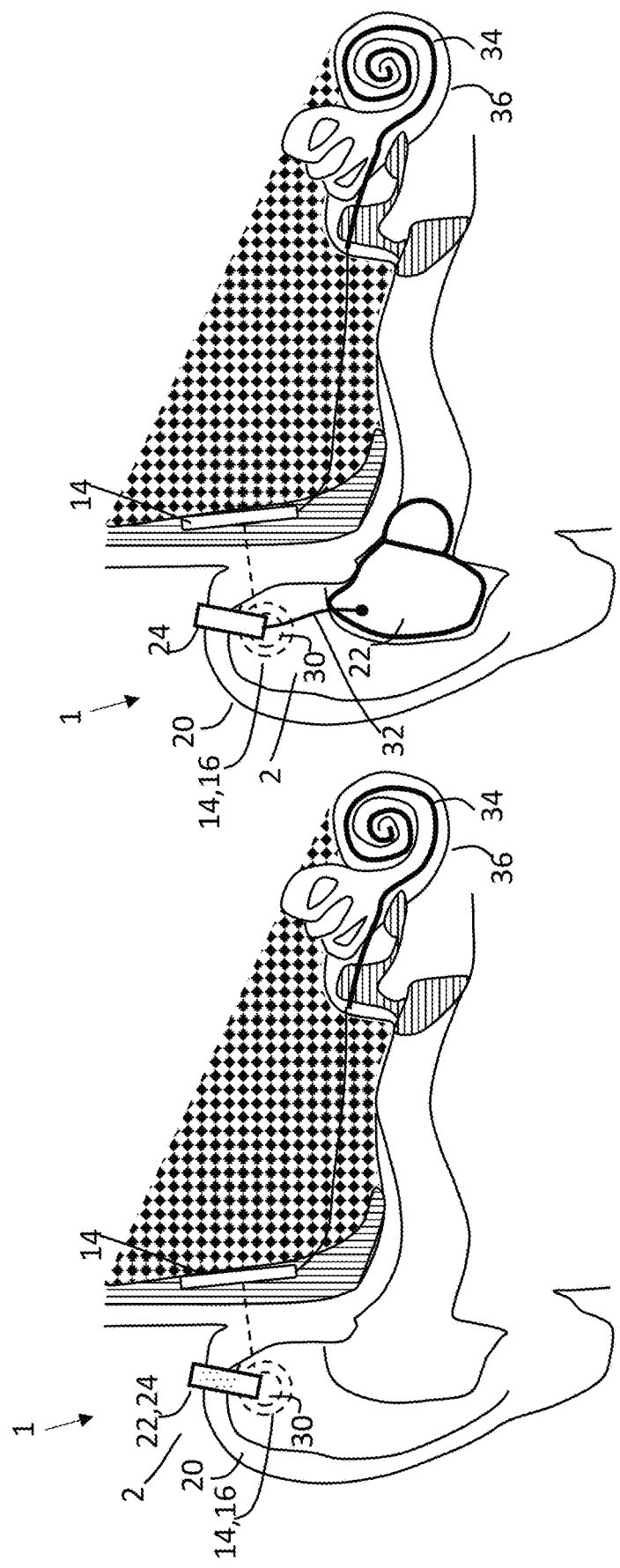

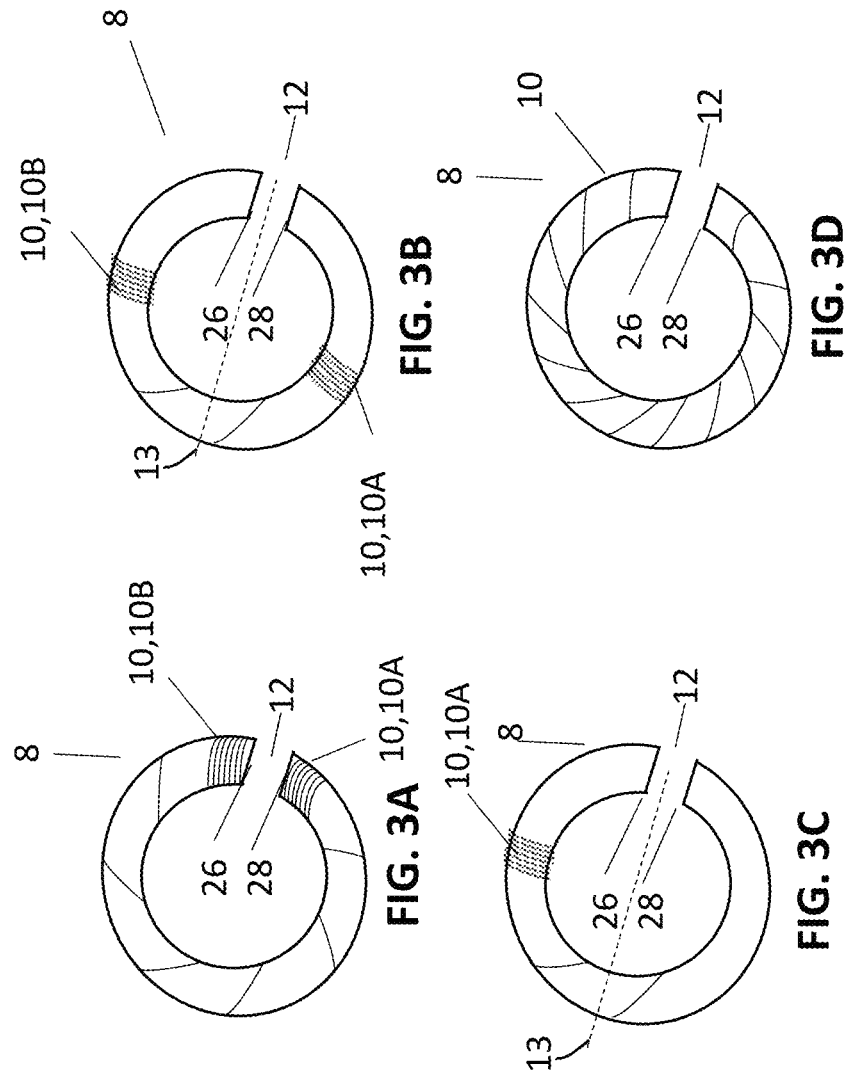

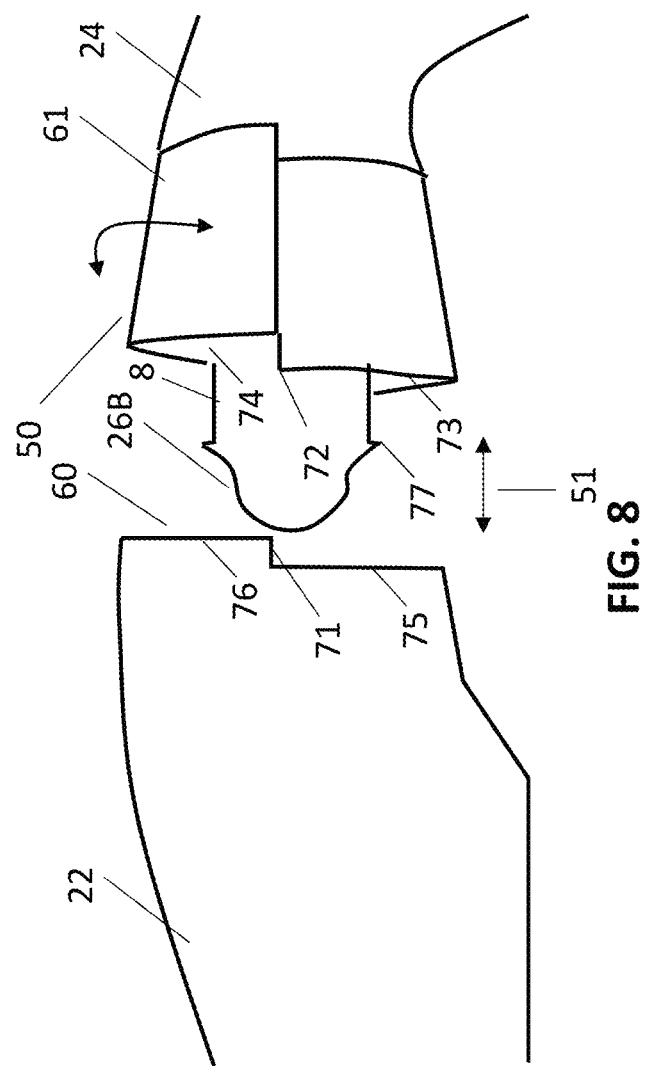

IMPLANTABLE HEARING AID SYSTEM COMPRISING A WIRELESS TRANSCUTANEOUS LINK

FIELD

The present disclosure relates to an implantable hearing aid system comprising a transcutaneous link. In particular, the disclosure relates to an implantable hearing aid system, comprising a wireless transcutaneous link for transmitting power and/or data signals over the link comprising a coupling between a first inductive coil arrangement of an external unit and a second inductive coil arrangement of an implantable unit, wherein a coupling coefficient between the coil arrangements is substantially improved.

BACKGROUND

Any discussion of the prior art throughout the specification in no way be considered as an admission that such prior art is widely known or forms parts of common general knowledge in the field.

A conventional implantable hearing aid system includes an external unit and an implantable unit, where the implantable unit is arranged between the skin and skull of a user of the system, and the external unit is arranged on to the skin and fixed to the implantable unit via magnetic forces. This implies that both the external unit and the implantable unit have a magnet. Implantable magnets associate with risks during MRI scan. As the patient enters the scanner, the powerful magnetic force of the scanner will attempt to force the implant magnet into alignment.

Many cochlear implant manufacturers use an open "soft silicone pocket" design, which uses a thin lip of silicone to hold a simple axial magnet in place.

With a soft silicone pocket design, there is minimal resistance to this powerful magnetic force, so the implant magnet can easily dislocate. A partially or fully dislocated implant magnet can cause extremely painful concentrated pressure. This often leads to incomplete scans and revision surgery to replace the magnet.

This is why magnet dislocation is the primary risk with cochlear implants. In an attempt to reduce the risk of magnet dislocation, companies with soft silicone pocket designs require a tight head bandage combined with a special rigid splint kit which makes the MRI scan complicated. The problem is that this tight head bandage does not eliminate the cause or the risk of magnet dislocation. Instead, this can put a painful pressure on the skin between partially dislocated implant magnet and the rigid splint. And the implant magnet can still dislocate and lead to revision surgery.

A solution to that is for example a rotatable, self-aligning implant magnet, however, the solution applies complicated mechanical design, and does not even guarantee high tesla MRI scan without any head bandage.

Furthermore, with a magnet in situ during a MRI scan will induce magnet-induced field distortions and consequent more pronounced artifacts preventing examination of a large area around the implant/magnet.

Furthermore, by fixating the external unit via magnetic forces causes a relatively high weight of the external unit, and also, a relatively large size of the external unit. This is not only uncomfortable for the user but also aesthetically unattractive. In addition, the implanted magnet has to be surgically removed or specially designed in case of MRI (Magnetic Resonance Imaging). Moreover, since the attractive forces between the magnets are limited, the external unit may move from the desired position and even fall down as a result of fast movements of the head (for example, when the patient jumps).

For a conventional coil arrangement where the transmitter coil and the receiver coil are arranged on either sides of the skin and in parallel planes, the coupling coefficient is very low because most of the magnetic field lines generated by transmitter coil is not picked up by the receiver coil, thus leading to poor energy transfer efficiency. In addition, as the two coils are located on either side of the skin, any change in coil separation, for example by way of increase in skin thickness, may result in rapid drop in the coupling coefficient between the two coils. In view of the efficiency problem, the external unit usually includes a relatively huge battery compartment or multiple batteries so that the implantable hearing aid system is useable for a usage period that doesn't cause annoyance for the user, for example requiring the user to frequently change batteries or recharge the battery compartment. Besides making the external unit aesthetically less appealing, the additional weight of the battery compartment or multiple batteries also require a stronger retention magnet that may possibly lead to discomfort and in extreme cases irritation or infection of the skin that is under constant magnetic attraction force generated between the retention magnet and implantable magnet.

For other types of hearing implants, other than cochlear implants, such as implants relying on bone-conduction for transmitting sound, a higher coupling coefficient can be used in two ways. Either the higher efficiency in power transmission through the skin is used to reduce the needed battery (and thereby reducing the size of the external sound processor) or used to elongate the battery lifetime (before recharge or battery change is needed). Importantly however, for bone conducting devices, the higher efficiency can be utilized for an increase of the Maximum Force Output or amplification. For bone conducting devices an increase in efficiency will directly translate into in increased amplification meaning that patients with more severe hearing loss can be treated.

Accordingly, the present disclosure provides an alternative coil arrangement for a wireless transcutaneous link and discloses an implantable hearing aid system that includes a wireless transcutaneous link where one or more of the above-mentioned shortcomings are addressed.

SUMMARY

An aspect of the disclosure is to provide an implantable hearing aid system which provides a more aesthetic look and less visibility.

Furthermore, an aspect of the disclosure is to provide a more efficient power transmission through the skin and between an external unit and an implantable unit of the implantable hearing aid system.

Additionally, an aspect of the disclosure is to provide an implantable hearing aid system which is more tolerant to strong external magnet fields, such as from an MRI scanner.

In addition, an implantable hearing aid system for bone conducting, the higher efficiency can be utilized to increase the amplification and a broadened inclusion criteria.

According to one or more of the mentioned aspects, an implantable hearing aid system is disclosed. The implantable hearing aid system includes an external unit which includes an electronic unit operationally coupled to a first inductive coil arrangement configured to transmit power and/or data signals, and where the first inductive coil arrangement includes a loop structure with coils wound around and along at least a part of length of the loop structure, and the loop structure comprises an opening. Furthermore, the implantable hearing aid system includes an implantable unit which comprises a second inductive coil arrangement configured to form a transcutaneous link with the loop structure and to receive the power and/or data signals over the transcutaneous link, and where the second inductive coil arrangement is configured to be implanted fully or partially within a part of an ear of a user of the implantable hearing aid system. The external unit includes a housing and an earhook, and where a first end-face of the loop structure is arranged within the earhook and a second end-face of the loop structure is arranged within the housing or within the earhook.

At least a part of the first inductive coil arrangement may be arranged within or vicinity to the through-going hole or opening of the second inductive coil arrangement when the external unit may be worn at the ear of the user. The through-going hole or opening may be denoted as a hollow section throughout the description.

The advantage of the implantable hearing aid system is that the external unit is not needed to be fixed to the implantable unit via a coupling magnet interface. A further effect is that the implantable hearing aid system is more tolerant towards strong magnetic fields, such as from an MRI scanner.

The external unit may be arranged on or in the ear providing a more aesthetic look as the external unit may either be hidden behind the ear of the user, in the ear of the user, or the external unit is small enough to be seen as a jewelry hanging on to the ear.

The external unit may be shaped as a conventional hearing aid, such as a Behind-The-Ear hearing aid, an In-The-Ear hearing aid, or as an earhook hearing aid. The housing of the external unit may include at least a microphone, the electronic unit, the first inductive coil arrangement or at least a part of the first inductive coil arrangement.

The housing of the external unit may comprise a processing unit configured to process an audio signal generated based on an acoustic signal received by the at least microphone in order to improve or augment the hearing capability of the user of the implantable hearing aid system.

The housing may comprise at least a microphone and the first inductive coil arrangement, and where the implantable unit includes the remaining components of a hearing aid, such as the processing unit, a transducer, a rechargeable battery etc.

The housing of the external unit may have a top part which includes the interface to the earhook, and the housing may further comprise a bottom part which is opposite to the top part.

The housing may have a first longitudinal axis along a longitudinal length from the top part to the bottom part, and the loop structure may have a second longitudinal axis along the length of the loop structure. The first longitudinal axis and the second longitudinal axis are not parallel.

The housing may be a behind-the-ear hearing aid, and the earhook may be bended in a direction not parallel to the first longitudinal axis, and the earhook may be bended such that the end-faces of the loop structure points directly or partially against each other. When the external unit is arranged on the ear and the implantable unit below the skin of the ear, the end-faces will be directed towards each other fully or partially and through the through-going hole or opening of the second inductive coil arrangement of the implantable unit. The earhook provides an ideal placement of the external unit behind the ear while also having an optimal position of the loop structure of the first inductive coil arrangement relative to the second inductive coil arrangement.

The earhook may be formed such that at least one of the end-faces of the loop structure is directed towards an outer surface of the housing, and the outer surface of the housing is directed towards the skin of the ear.

The housing may have an area which has an inner surface and an outer surface, and the inner surface is arranged opposite to the outer surface. At least one of the end-faces of the loop structure is directed towards the inner surface of the area, and at least one of the end-faces of the loop structure is directed towards the outer surface, and the two end-faces are directed towards each other fully or partially.

The through going hole or opening may form part of a hollow section of the second inductive coil arrangement.

When the user is wearing the implantable hearing aid system, the external unit may be arranged on or in the ear of the user, and part of the implantable unit may be arranged between the skin and the skull of the user, and the second inductive coil arrangement may be arranged fully or partially below the skin of the ear of the user. The external unit may be configured to transmit power and/or data signals via the first inductive coil arrangement and through the skin of the ear and to the second inductive coil arrangement.

The implantable unit may be configured to transmit power and/or data signal via the second inductive coil arrangement and through the skin of the ear and to the first inductive coil arrangement.

The housing may be connected to the earhook via a connector part. The connector part may comprise one or more wires for transmitting power and/or data signals between the loop structure of the earhook and the electronic unit of the housing. The one or more wires connects the loop structure and the electronic unit and/or other units of the external unit.

The housing may be arranged behind the ear or in the ear of the user while the earhook is fixed to the ear by a clamping force or via a piercing in the skin.

The housing and the earhook may be connected via a flexible unit. The flexible unit is configured to apply the earhook into a first position or at least a second position when applying a force onto the earhook or the housing. In the first position, the external unit is not fasten onto the ear, and thereby, the user is able to remove the external unit from the ear. In the second position, the external unit is fasten to the ear by a clamping force between the housing and the earhook. By fastening the external unit to the ear does not mean that the external unit is permanently fasten to the ear. The user of the system may detach the external unit in any examples of the external unit. The detaching of the external unit may be done by changing the position of the earhook or by changing the position of the end-faces of the loop structure. For example, when the end-faces of the loop structure are engaged, the earhook can not be taken off, and when the end-faces are disengaged the earhook can be removed.

The flexible unit may be that the earhook or part of the earhook is made of a resilient material, such as silicone, and which makes the earhook moveable in a direction which makes it easier for the user to remove the earhook off the ear.

The flexible unit may include a rotating mean which is configured to rotate the earhook or at least a part of the earhook between the first position and at least the second position.

The size of the opening of the loop structure can be adjusted in terms of changing the position of the earhook between the first position and at least the second position.

The size of the opening determines the clamping force between the external unit and the ear.

The housing and the earhook may be merged, and the housing may be made of a first material and the earhook may be made of a second material, wherein the second material may be more flexible than the first material. The first material allows the earhook to be moved into the first position or the second position while applying a force onto the earhook or the housing. In the second position the external unit is fasten to the ear by a clamping force between the housing and the earhook onto the ear.

The clamping force may be provided by the flexible unit or the material which the earhook may be made of.

The loop structure may comprise a first loop structure which may be arranged within the housing and a second loop structure which may be arranged within the earhook, and both the first loop structure and the second loop structure forms the loop structure. The first loop structure and the second loop structure may be connected such that the first loop structure is moveable relative to the second loop structure and transferring a substantial number of magnetic field lines in between the first loop structure and the second loop structure. The first loop structure may comprise the second end-face and the second loop structure may comprise the first end-face.

The loop structure may be arranged within a protective sleeve for protecting the ferrite material of the loop structure.

The first inductive coil arrangement may include a protection cover configured to comprise the loop structure and the coils wound around the loop structure. The protection cover may be made of a silicone material or any kind of material which protects the loop structure with minimal reduction of the inductive coupling efficiency between the first and the second inductive coil arrangement. The purpose of the protection cover is to protect the loop structure from being damaged if the first inductive coil arrangement falls off the ear.

The loop structure may consist of a magnetic core of a ferromagnetic material, such as laminated iron, iron powder, or ferrite, around which wire is wound around. The shape of the loop structure may be toroidal with a through-going hole in a center of the loop structure, and where the magnetic core circumference the though hole.

The loop structure may be toroidal with a circular, elliptical, rectangular, square, polygonal shape, curved shape or any combination thereof.

The loop structure may include shape that is selected from a circular, elliptical, rectangular, square, polygonal shape, curved shape or any combination thereof.

The coils wound around a part of the loop structure may be arranged within the earhook, i.e. outside the housing of the external unit, for the purpose of protecting the electronic unit and/or other units of the external unit which are sensitive to external and unwanted external electromagnetic fields provided by the first inductive coil arrangement.

The external unit may include a shielding unit configured to magnetically shield the electronic unit and other units of the external unit from unwanted external electromagnetic fields provided by the first inductive coil arrangement. The shielding unit may be a resonant element being provided within a near field of the loop structure, the resonant element being connected to the ground potential through energy dissipating means to terminate and dissipate electromagnetic noise from at least a part of the loop structure. The shielding unit may be arranged between the loop structure and the electronic unit and the other units of the external unit. The resonant element implements a notch filter filtering the electromagnetic radiation noise.

The term "other units of the external unit" includes one or more of processing unit, rechargeable battery, control units, communication units, RF antenna, other antenna types, speaker, microphone etc.

The resonant element is connected to the ground potential through a battery of the external unit.

A winding density of the coils along the loop structure of the first inductive coil arrangement may be higher in the vicinity of the first end-face and the second end-face of the loop structure as compared to the remaining parts of the loop structure. The purpose of the higher density is to provide a more focus magnetic field lines between the end-faces of the loop structure of the first inductive coil arrangement and through the through-going opening of the second inductive coil arrangement. More focused magnetic field lines provide a more efficient transcutaneous link in respect to energy transfer between the first and second inductive coil arrangements.

The winding density of the coils along the loop structure of the first inductive coil arrangement may be equally or partially equally along the length of the loop structure.

The implantable unit may be an implantable processor and/or an implantable stimulator that is configured to generate an output. The output may be configured to generate perceivable stimulation for the user. For example, such perceivable stimulation includes perception of sound in case of implantable hearing aids. For the implantable hearing aid system, the output may include a stimulation pulse (usually frequency specific) or signal for generating vibrational force (usually frequency specific). In an embodiment, the implantable unit comprises a power controller adapted to control utilization of power received at the second inductive coil arrangement.

The data signals being transmitted via the transcutaneous link may include control signals, configuration signals, information signals and/or audio signals, and the implantable unit may comprise a transducer, such as a vibration-based transducer and/or an electrical stimulator, for generating, based on the audio signals, vibration and/or electrical stimulation, respectively. The vibration is transmitted onto the skull of the user via a fixture or via a housing of the vibration. The electrical stimulation is applied to the cochlea of the user via an electrode array which comprises a plurality of electrodes arranged within the cochlea of the user. The vibration-based transducer may be an electromagnetic based transducer, or a piezoelectric based transducer.

The second inductive coil arrangement may be within an implantable housing which comprises the transducer or within an implantable coil housing which is connected via one or more wires to the implantable housing. The implantable coil housing may be arranged below the skin of the ear of the user, and the implantable housing may be arranged between the skin and the skull of the user.

The implantable coil housing, the implantable housing or the second inductive coil arrangement may comprise an implantable loop structure with coils wound around along at least a part of length of the implantable loop structure, and a through-going hole which may be configured to have an overlapping interface with the first inductive coil arrangement and/or the loop structure of the first inductive coil arrangement.

When the implantable unit is arranged below the skin of the ear, the radius or diagonal of the through-going hole or opening of the second inductive coil arrangement may be partially or nearly parallel with the skin of the ear, and the depth of the through-going hole or opening may be partially or nearly orthogonal to the skin of the ear.

The through-going hole or opening of the implantable housing may have an inner side which is chamfered or partially chamfered. The purpose of the chamfered inner side is to guide the loop structure of the external unit into an optimal position when positioning the earhook onto the ear. When being in the optimal position, an optimal inductive connection is provided between the end-faces of the loop structure and the implantable loop structure. The chamfered inner side is angled to an extend which directs the loop structure towards the center of the through-going hole of the second inductive coil arrangement while applying the earhook to the ear.

The earhook may have a tip which may be configured to have an overlapping interface with the second inductive coil arrangement. The tip may comprise a part of the loop structure, for example one of the end-faces of the loop structure.

Either the first or the second end-face of the loop structure of the first inductive coil arrangement may be configured to have an overlapping interface with the second inductive coil arrangement.

The overlapping interface may be arranged within the through-going hole or an area circumference by the chamfered inner side.

The overlapping interface provides an improved optimal inductive connection as the distance between the end-faces of the loop structure and the implantable loop structure is reduced.

The transcutaneous link may be an inductive link which may be bidirectional or unidirectional.

At least a part of the second inductive coil arrangement may be arranged in at least one of the following parts of the ear: Helix, Antihelix, Scapha, Triangular fossa, Pinna, Auricular lobule(earlobe), and Concha. By arranging an implantable unit, or to be more specific, the second inductive coil arrangement, within the ear results in a significant reduction in distance between the first and second inductive coil arrangement in comparison to arranging the implantable unit in the head, i.e. between the skull and skin, of a patient. The reduction in distance provides in a more efficient coupling between the first and the second inductive coil arrangement.

The end-faces of the loop structure may be merged together forming a closed loop structure having a geometrical shape that includes a closed curve, wherein a point moving along the closed curve forms a path from a starting point to a final point that coincides with the starting point when the closed curve is in a closed mode. In one embodiment, the closed curve may include a single part loop structure comprising an openable section that includes the first end-face and a second end-face. The openable section is attached to the rest of the section of the loop structure at the first end-face end and is adapted to open the openable section at the second end-face end (i.e. an open mode is defined when the openable section is open) to allow access to a hollow section, i.e. a through-going hole or opening, of the first inductive coil arrangement and positioning of the part of the ear within the hollow section. The closed mode is defined when the openable section is engaged with rest of the section at the second end-face to form the closed curve.

The loop structure may be in one piece.

The loop structure may be in one piece and which may be moveable together with the earhook. The tip of the earhook may be made of a resilient material which makes it easier for the user to apply or remove the earhook onto the ear.

The loop structure may include multi-parts loop structure wherein the multi-parts includes a plurality of detachable parts, such as a first sub-part and a second sub-part, that are configured to attach with one another to form a closed loop structure. The closed mode is defined when the plurality of detachable parts is attached to one another. Accordingly, an open mode may be defined when the plurality of detachable parts is not attached to one another and in the open mode, the loop structure is adapted to allow positioning of the part of the body part within the hollow section of the loop structure. This may be achieved when the loop structure is in the open mode.

The loop structure may be defined by a geometrical shape that includes an open curve, defining an open loop structure, wherein a point moving along the open curve forms a path from a starting point to a final point that is proximal to but separated from the starting point by a distance. The distance is typically a function of a thickness of the body tissue and/or skin to which the loop structure is attached, i.e. the distance is configured such that the loop structure is attachable to the user's ear. The distance is defined between the first end-face and the second end-face. The distance is selected from a group consisting of a length that is smaller than the thickness of the ear tissue, a length that is more than the thickness of the ear tissue but is adapted to be reduced such that the changed length is smaller than the thickness of the ear tissue, and a length that is less (may even be close to zero) than the thickness of the ear tissue but is adapted to be increased such that the changed length is slightly smaller than the thickness of the ear tissue. It is apparent that the length smaller or slightly smaller than the thickness of the ear tissue is adapted in a way such that a compressive retention force between a first end face (i.e. first point of the geometrical shape) and a second end-face (i.e. second point of the geometrical shape) against the body tissue is applied.

It is apparent that the length of the opening is smaller or slightly smaller than the thickness of the ear tissue and the second inductive coil arrangement. Or, the length of the opening may be adapted in a way such that a compressive retention force between a tip of the earhook and the housing (or between the end-faces of the loop structure) of the external unit against the ear tissue is applied. The skilled person would appreciate that the distance may be changed in order to achieve a balance between reliable retention and user comfort, especially for extended wearing of the external unit.

The earhook may comprise a tip with a compression reducing mean, and wherein the tip is configured to touch the skin of the part of the ear when the external unit is worn by the user. The advantage with the compression reducing mean is that the comfort of wearing the earhook is improved, and the earhook is adaptable to different ear type, such as with different ear thickness and/or ear form.

The compression reducing mean may include a spring configured to be compressed when the tip is touching the skin.

The compression reducing mean may be made of a resilient material, such as foam or silicone.

The tip could be made of a slow-recovery foam in order to reduces the pressure on skin, the shape of the tip should also be optimized for best retainment and comfort. For example, it could be made more flatter and have a high friction characteristic.

The term "proximal" or "vicinity" to the second inductive coil arrangement indicates that the first inductive coil arrangement is arranged close to the second inductive coil arrangement such that an inductive coupling between the first inductive coil arrangement and the second inductive coil arrangement is achieved. This is achieved when the loop structure is attached to the ear.

The term "hollow section" or "through-going hole or opening are defined by an area that is enclosed by the closed loop structure when the closed loop structure is in the closed mode.

The term "hollow section" or "through-going hole or opening may be defined by an area that the loop structure in combination with an imaginary line joining the distance separating the first end-face and the second end-face.

The external unit may include a first RF antenna configured to communicate with a second antenna arranged within the implantable unit, and thereby data signals may be communicated via the communication between the first and the second RF antenna, and power signals may be transmitted by the first inductive coil arrangement to the second inductive coil arrangement. This is advantages to communicate the power signals and the data signals by separate communication interfaces, such as the RF and inductive interface. The RF link between the first and the second RF antenna may be based on Bluetooth, Bluetooth Low Energy, or other kind of short-range communication protocols.

The external unit may be configured to communicate the power signals and the data signals via the inductive coil arrangements in different communication modes, where in a first communication mode the data signal is transmitted to the implantable unit and in a second communication the power signal is transmitted to the implantable unit. In the respective communication modes a resonance frequency of the inductive coil arrangement may be different and/or, the modulation of the power signals and the data signals may be different.

Throughout the specification, unless stated explicitly otherwise, different disclosed embodiments should be considered combinable.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIGS. 1A to 1E illustrate different examples of an implantable hearing aid system;

FIGS. 3A to 3D illustrate different examples of the loop structure:

FIG. 8 illustrates an example of the external unit;

DETAILED DESCRIPTION

Figure 1A:
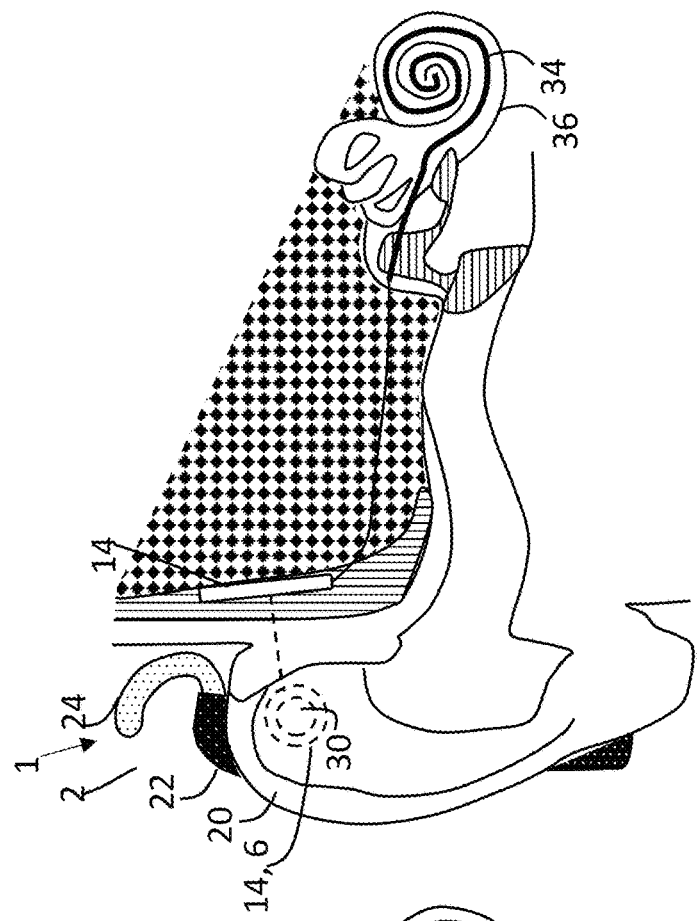

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, etc. (collectively referred to as "elements"). Depending upon particular application, design constraints or other reasons, these elements may be implemented using other equivalent elements.

A hearing aid is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. Such audible signals may be provided in the form of an acoustic signal transferred as mechanical vibrations to the user's inner ears through bone structure of the user's head.

The hearing aid may be replaced by a system comprising one or two hearing aids, and a "binaural hearing system" refers to a system comprising two hearing aids where the devices are adapted to cooperatively provide audible signals to both of the user's ears or the hearing aid of bone conduction type may be part of a bimodal system comprising a cochlea implant and a bone conduction hearing aid. The system may further include auxiliary device(s) that communicates with at least one hearing aid, the auxiliary device affecting the operation of the hearing aids and/or benefitting from the functioning of the hearing aids. A wired or wireless communication link between the at least one hearing aid and the auxiliary device is established that allows for exchanging information (e.g. control and status signals, possibly audio signals) between the at least one hearing aid and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing aid. The remote control is adapted to control functionality and operation of the at least one hearing aids. The function of the remote control may be implemented in a SmartPhone or other electronic device, the SmartPhone/electronic device possibly running an application that controls functionality of the at least one hearing aid.

In general, a hearing aid includes i) an input unit such as a microphone for receiving an acoustic signal from a user's surroundings and providing a corresponding input audio signal, and/or ii) a receiving unit for electronically receiving an input audio signal. The hearing aid further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer for providing mechanical vibrations either transcutaneously or percutaneously to the skull bone.

FIGS. 1A to 1E illustrate different examples of an implantable hearing aid system 1. The implantable hearing aid system 1 comprises an external unit 2 including an electronic unit 4 (not shown) operationally coupled to a first inductive coil arrangement 6 (not shown) configured to transmit power and/or data signals. Furthermore, the implantable hearing aid system comprises an implantable unit 14 which includes a second inductive coil arrangement 16 (not shown) configured to form a transcutaneous link 18 (not shown) with the first inductive coil arrangement 6 (not shown). The second inductive coil arrangement 16 is implanted within a part of an ear 20 of a user of the implantable hearing aid system 1. The second inductive coil arrangement 16 has a hollow section 30 which is configured to receive a part of the earhook 24. The external unit includes a housing 22 and an earhook 24, and where the first inductive coil arrangement may be arranged within the earhook 24 or partially within the earhook 24 and partially within the housing 22.

The implantable unit 14 may include an implantable stimulator and/or an implantable vibrator. In the specific examples of FIGS. 1A to 1E, the implantable unit 14 includes an implantable stimulator which has an electrode array 34 for providing electrical stimulation to a cochlea 36 of the user.

FIG. 1A illustrates an example of the implantable hearing aid system 1 where the housing 22 is shaped as a Behind-The-Ear hearing aid with the earhook 24 attached onto. The earhook 24 goes around the top part of the ear 20 and applies a compression force between the earhook 24 and the housing 22 onto the skin of the ear 20. A part of the earhook 24 is arranged proximal to the hollow section 30. The hollow section 30 may be denoted as a through-going hole or opening.

Figure 1B:
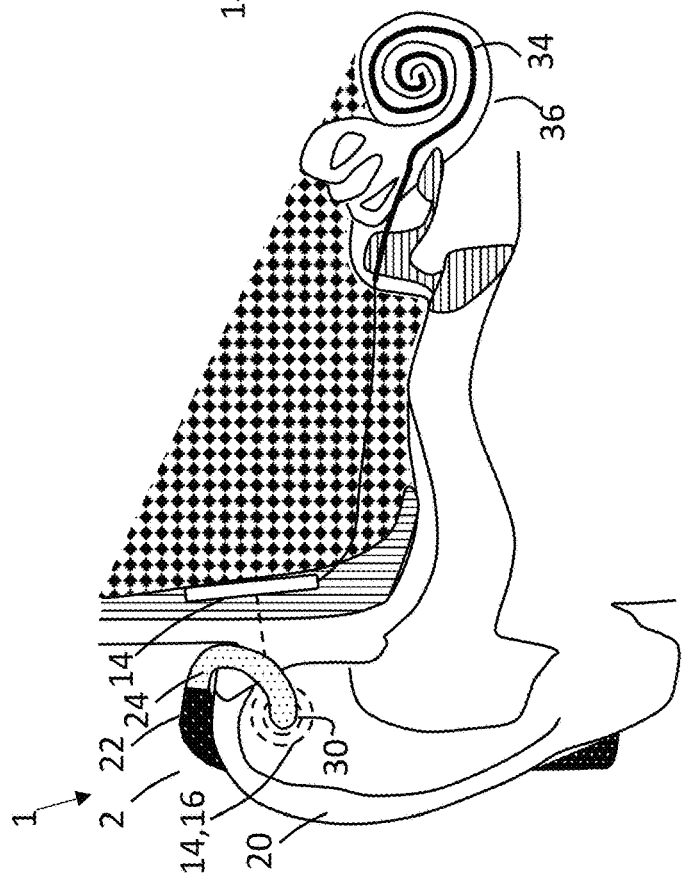

FIG. 1B illustrates an example of the implantable hearing aid system 1 where the earhook is in a position which makes it possible for the user to remove the external unit 2 off the ear 20.

FIG. 1C illustrates an example of the implantable hearing aid system 1 where the housing 22 and the earhook 24 are merged. The implantable unit 14 includes one or more of the following components: a processor unit, an implantable transducer and/or an implantable stimulator unit, a memory and a rechargeable battery 22. The external unit 2 includes one or more of the following components: a processor unit, an implantable transducer and/or an implantable stimulator unit, a memory and a rechargeable battery 22. In this specific example the external unit 2 includes a microphone and circuitry for driving the microphone, the earhook 24 and the housing 22, and the implantable unit 14 includes the second inductive coil arrangement 16 a processor unit, an implantable stimulator unit, a memory and a rechargeable battery. In this specific example, the size of the external unit 2 has reduced significantly in comparison to the example described in FIGS. 1A and 1B.

FIG. 1D illustrates an example of the implantable hearing aid system 1 where the housing 22 is shaped as an In-The-Ear hearing aid, and the housing 22 is connected to the earhook 24 via a connector part 32 which may include one or more wires for transmitting power and/or data signals between the first inductive coil arrangement 6 (not shown) of the earhook 24 and the electronic unit 4 (not shown) of the housing 22. The earhook 24 may be attach to the ear 20 by a clamping force provided by a clamping mean (not shown) forming part of the earhook 24.

The earhook 24 may include a needle which is configured to penetrate the ear 20 for fixating the earhook 24 to the ear 20.

Figure 1E:
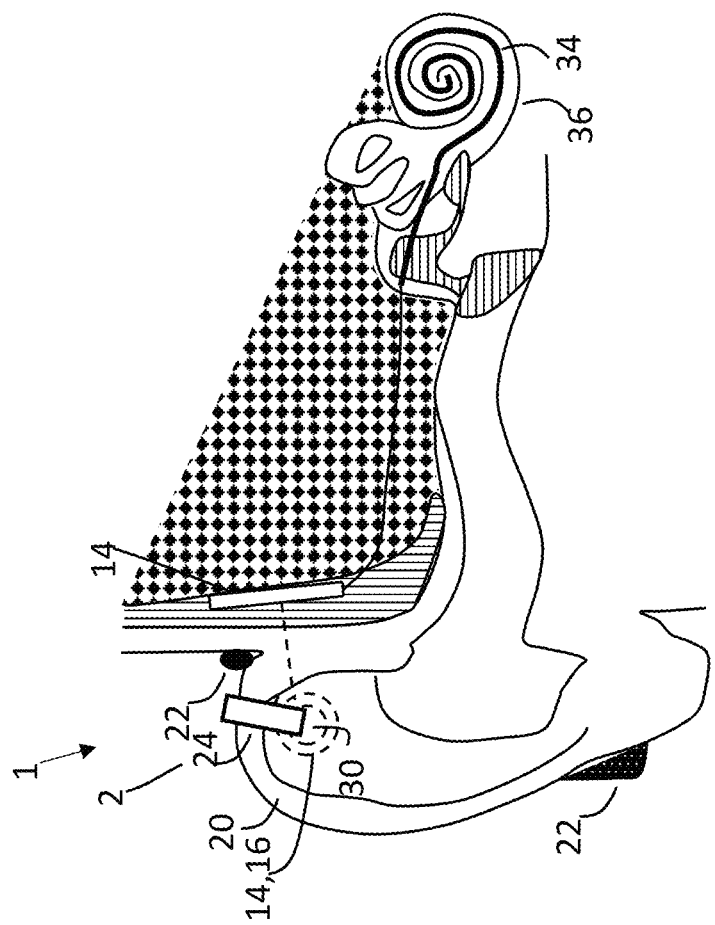

FIG. 1E illustrates an example of the implantable hearing aid system 1 where the housing 22 is shaped as a Behind-The-Ear hearing aid. The earhook 24 is connected to the housing via a connector part 32 (not shown), and the earhook 24 may be attach to the ear 20 by a clamping force provided by a clamping mean (not shown) forming part of the earhook 24.

The earhook 24 may include a needle which is configured to penetrate the ear 20 for fixating the earhook 24 to the ear 20.

Figure 2B:
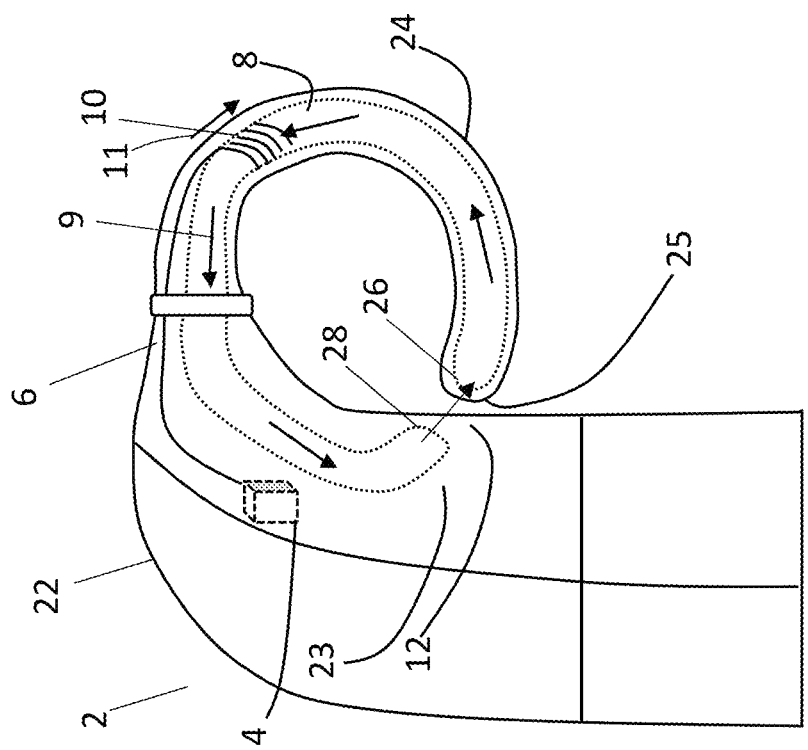
FIGS. 2A to 2F illustrate different examples of the external unit.
Figure 2A:
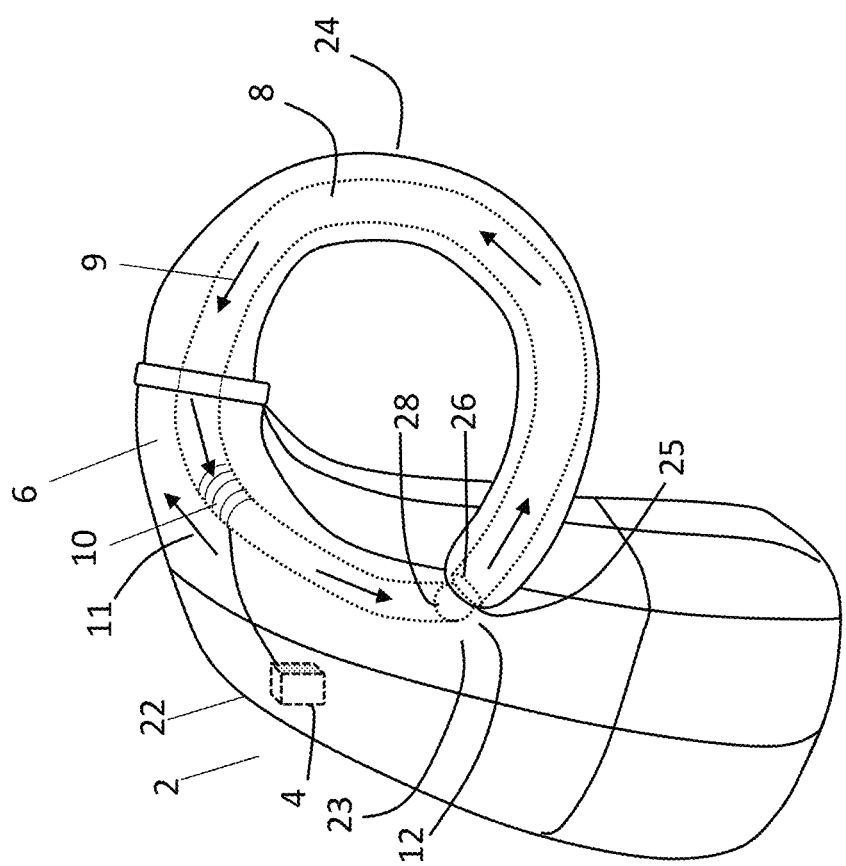

FIGS. 2A to 2F illustrate different examples of the external unit 2 comprising the earhook 24 with the loop structure 8 and the electronic unit 4 arranged within the housing. FIG. 2A illustrates a specific example of the external unit 2 where the housing 22 is a behind-the ear hearing aid and connected to the earhook 24. The loop structure 8 is partly arranged within the housing 22 and partly within the earhook 24 and where the loops 10 are arranged on the part of the loop structure which is within the housing 22. Between the first end-face 26 and the second end-face 28 an opening 12 is formed for receiving a part of the ear 20 and the second inductive coil arrangement 16. The current 11 applied to the coils 10 travels in an opposite direction as magnetic field lines 9 within the loop structure 8, and when the external unit 2 is worn by the use, the magnetic field lines 9 travels through a hollow section of the second inductive coil arrangement 16 (not shown) which is part of the implantable unit 14 (not shown).

FIG. 2B illustrates a similar external unit 2 as described in FIG. 2A, however, the coils 10 are arranged within the earhook because of increasing the distance between the coils 10 and other units of the external unit 2. Furthermore, the opening 12 between the end-faces (26, 28) or the outer surface 23 of the housing 22 and a tip 25 of the earhook is clear seen.

Figure 2E:
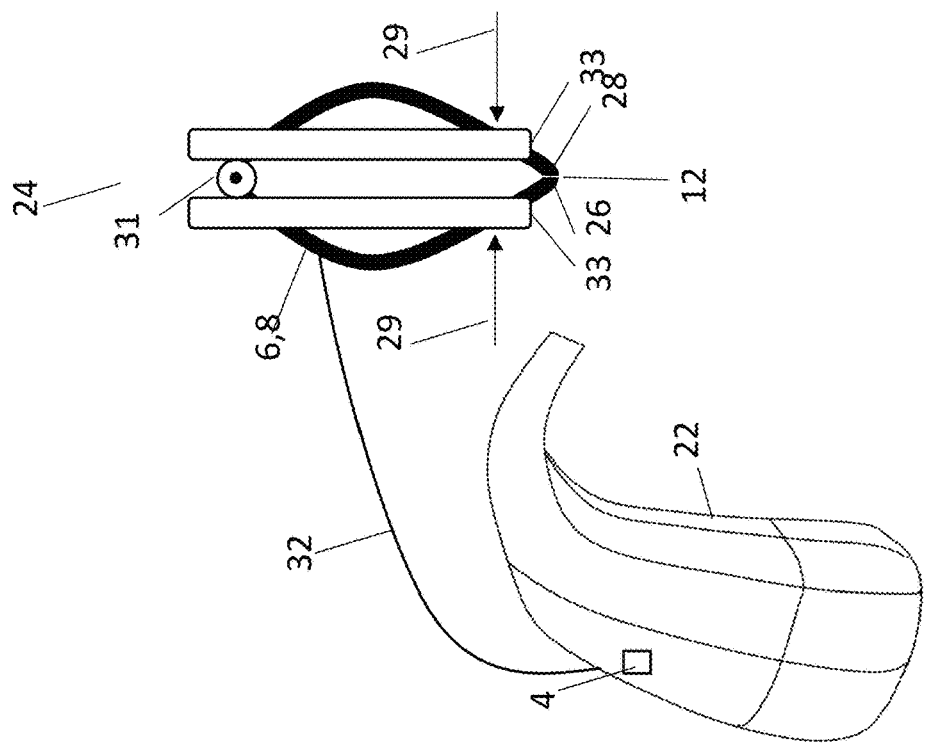
Figure 2D:
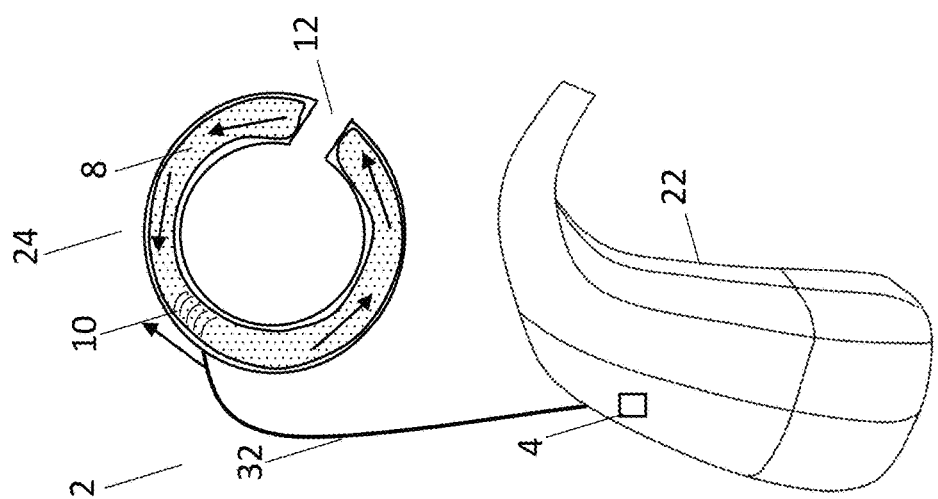
Figure 2C:
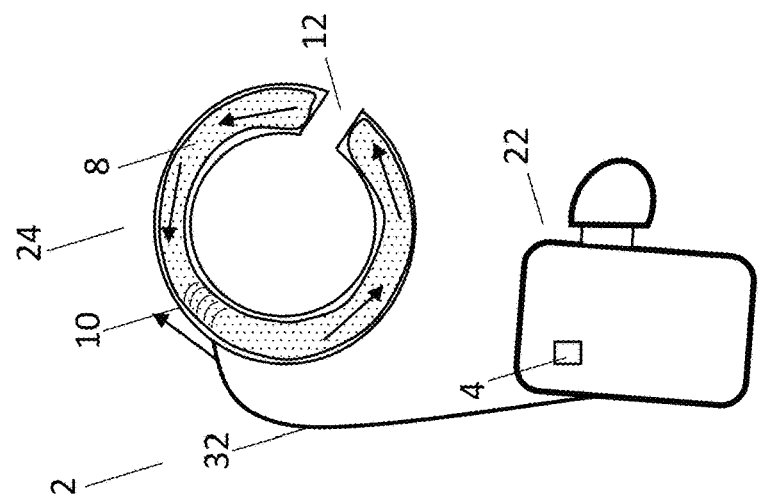

FIG. 2C illustrates a specific example of the external unit 2 where the housing 22 is an in-the-ear hearing aid and connected to the earhook 24 via a connector part 32 which comprises one or more wires for transmitting current to the coils 10 and power and/or data signals to be communicated to the implantable unit 14 via the transcutaneuous link 18. The earhook 24 is a separate part to the housing 22, where the housing 22 is arranged into the ear canal of the user and the earhook 24 is applied onto the ear such that the opening 12 receives a part of the ear 20 of the user.

The external unit 2 in FIG. 2D is similar to the external unit 2 illustrated in FIG. 2C, however, the housing 22 is a behind-the-ear hearing aid. FIG. 2E illustrates a similar external unit 2 to the one illustrated in FIG. 2D, however, the earhook is configured to be fixed on the ear by a clamping force between at least the end-faces (26, 28) of the loop structure 8. The clamping force is provided by clamping means 33 which the first inductive coil arrangement 6 is applied onto and a spring unit 31.

Figure 2F:
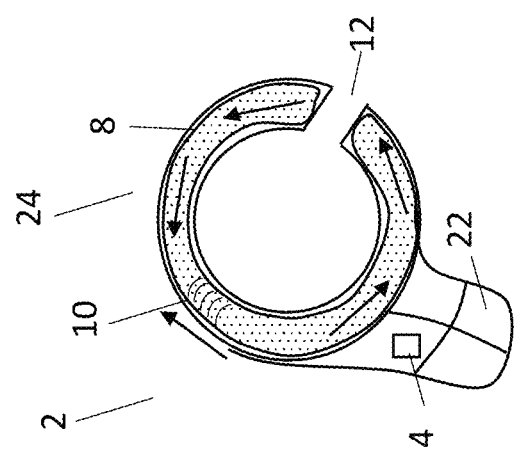

FIG. 2F illustrates a specific example of the external unit 2 where the housing 22 is merged with the earhook 24 such that when the external unit 2 is placed onto the ear both housing 22 and the earhook 24 are arranged on the pinna of the ear 20. In this example, the implantable unit 14 includes a rechargeable battery, a processor unit and other units to drive the implantable unit 14 together with the external unit 2. The external unit 2 includes at least one microphone, the electronic unit 4 and the first inductive coil arrangement 6.

FIGS. 3A to 3D illustrate different examples of the loop structure 8. In FIG. 3A two groups of coils (10, 10A, 10B) are applied such that the density of the coils at the end-faces (26, 28) of the loop structure 8 is higher than in the remaining parts of the loop structure. In FIG. 3B, the loop structure 8 is symmetric around a symmetry axis 13, and the two groups of coils (10, 10A, 10B) are arranged at different positions on the loop structure 8 and on each side of the symmetry axis 13. FIG. 3C illustrates a single group of coils (10, 10A) arranged on one side of the symmetry axis 13, and in one example the single group of coils (10, 10A) is arranged in the earhook 24 and outside the housing 22. FIG. 3D illustrates the coils 10 being distributed along the loop structure 8 with a density being the same or partially the same.

Figure 4A:
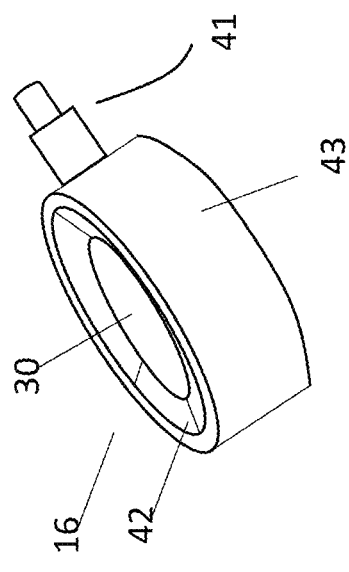
FIGS. 4A and 4B illustrate an implantable coil housing.
Figure 4B:
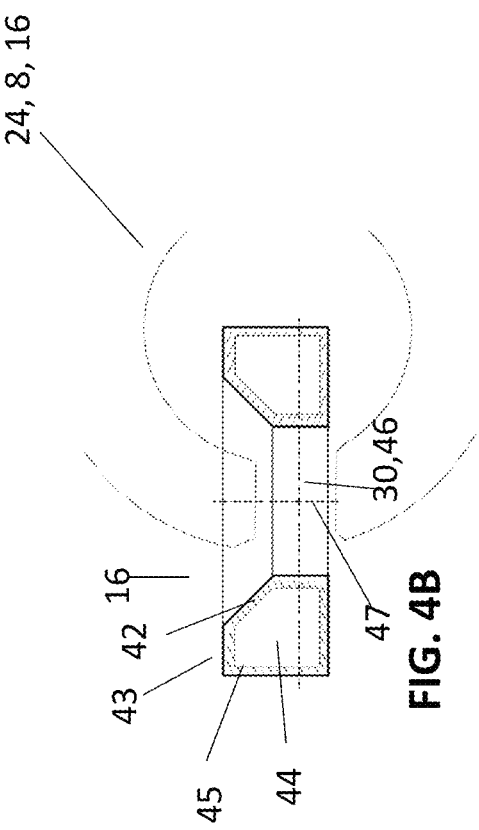

FIGS. 4A and 4B illustrate an example of the second inductive coil arrangement 16. The second inductive coil arrangement 16 includes an implantable coil housing 43 which has a hollow section 30 with a chamfered inner side 42. In another example, the hollow section may have an inner side which is straight. The chamfered inner side 42 is configured to guide the first inductive coil arrangement 6 for obtaining an optimal position of the loop structure 8 relative to the hollow section 30 of the second inductive coil arrangement 16. A straight inner side provides a more fixed connection between the first inductive coil arrangement 6 and the second inductive coil arrangement 16. The hollow section 30 may be tube shaped or box shaped or any shape which allows optimal inductive connection between the first 6 and the second 16 inductive coil arrangement.

FIG. 4A illustrates an implantable coil housing 43 which has a connection interface 41 to an implantable housing 14 (not shown). The implantable coil housing 43 may be arranged below the skin of the user, and the implantable housing may be arranged between the skin and the skull of the user. The implantable housing may include the transducer, such as a vibration-based transducer and/or an electrical stimulator. FIG. 4B illustrates a cross section of the implantable coil housing 43. Within the implantable coil housing 43 a loop structure 44 is shown with coils 45 wound around a length of the loop structure 44

The implantable coil housing 43 has a first axis 46 which is parallel or partially parallel with the skin of the ear when the second inductive coil arrangement 16 is arranged below the skin of the ear 20 of the user. The radius or the diagonal of the hollow section is parallel with the first axis 46. The implantable coil housing 43 has a second axis 47 which is parallel to the first axis 46 and centrally arranged in the hollow section 30. When the end-faces (26, 28) are aligned with the second axis 47 an optimal inductive connection is obtained between the first 6 and the second 16 inductive coil arrangement.

Figure 5:
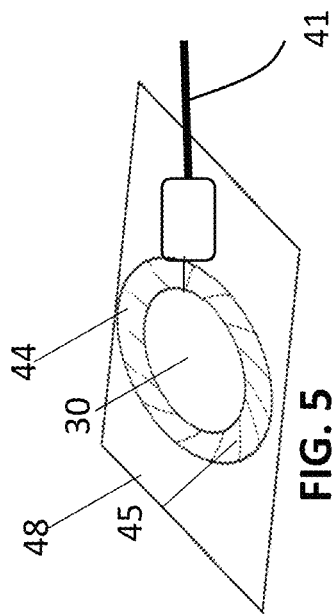
FIG. 5 illustrates an example of the second inductive coil arrangement.

FIG. 5 illustrates an example of the second inductive coil arrangement 16 being integrated into a printed circuit board (PCB) 48. Implementing the second inductive coil arrangement 16 into a PCB is for reducing the size of the coil arrangement 16.

Figure 6B:
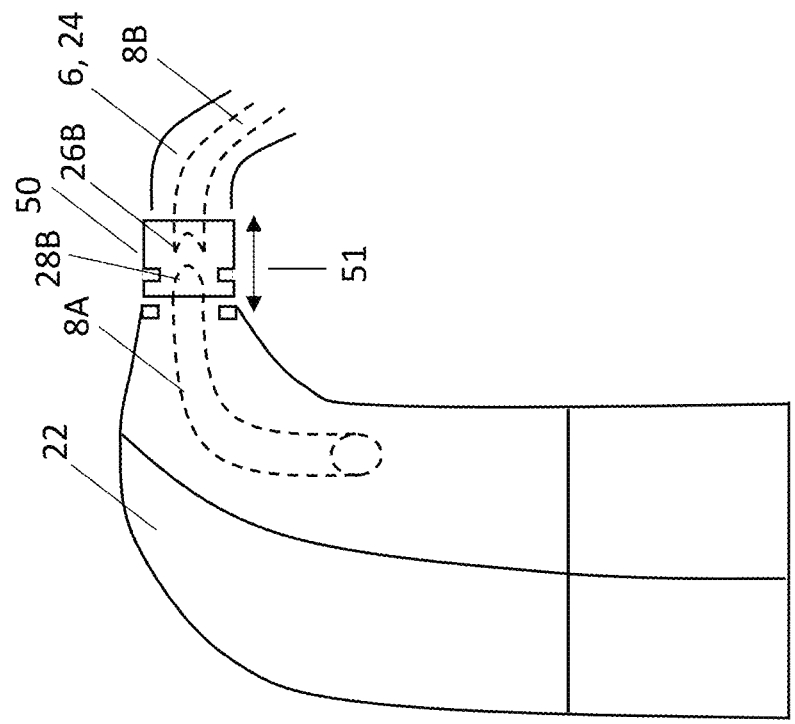
FIGS. 6A to 6D illustrate different examples of a flexible unit.
Figure 6A:
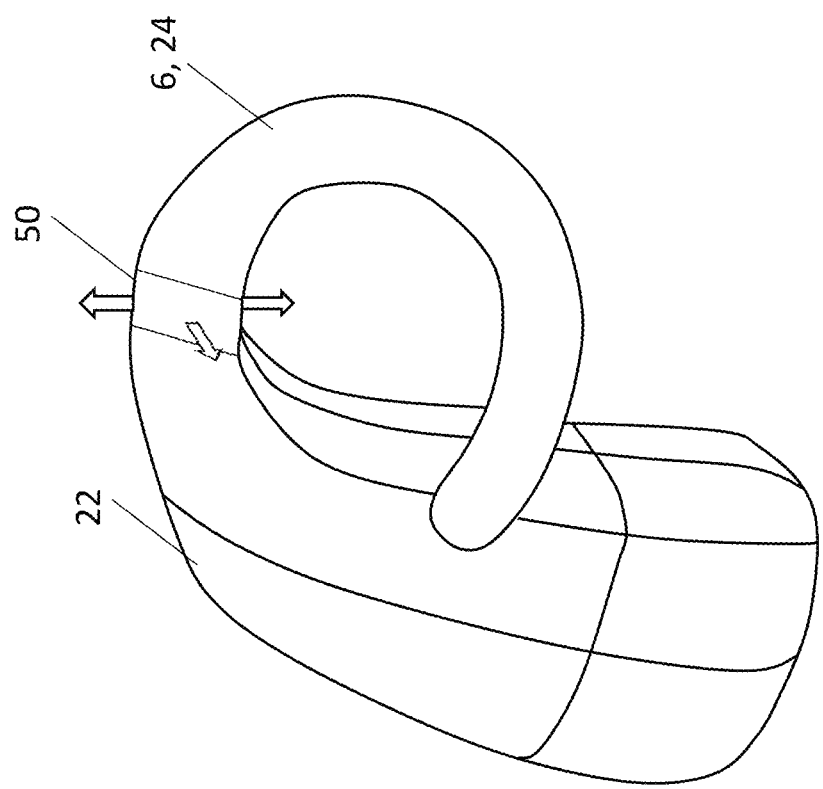

FIGS. 6A to 6D illustrates different examples of a flexible unit 50 configured for providing a flexible connection between the housing 22 and the earhook 24. In FIG. 6A, the flexible unit 50 is configured to move the earhook 24 in any directions which will result in an ideal position of both housing 22 and the earhook 24 onto the ear 20 of the user. For example, when moving the earhook 24 from a first position to a second position by applying a force to the earhook 24, and release the force, the earhook 24 may either be kept in the second position or will return back to the first position. The second position of earhook 24 may be suitable for removing the external unit 2 from the ear 20, and the first position of the earhook 24 may be suitable for obtaining an optimal connection between the first inductive coil arrangement 6 and the second inductive coil arrangement 16.

In FIG. 6B the flexible unit 50 is configured to be snap coupled to the housing 22 and the earhook 24, or in another example, the flexible unit 50 may be moulded into either the housing 22 or the earhook 24 and then snap coupled to either the housing 22 or the earhook 24. The loop structure 8 comprises a first loop structure 8A which is be arranged within the housing 22 and a second loop structure 8B which is arranged within the earhook 24, and both the first loop structure 8A and the second loop structure 8B forms the loop structure 8. Within the flexible unit 50 another first end-face 26B of the loop structure and another second end-face 28B of the loop structure 8 are flexible connected, and the flexible connection provides that the first loop structure 8A and the second loop structure 8B are moveable relative to each other in a direction not parallel to an insertion direction 51 of the flexible unit 50. One example for obtaining the flexible connection is for example by adapting the shape of one of the end-faces (26B, 28B) to fit with the shape of the another end-face (26, 28). If the another first end-face 26B is for example round shaped then the another second end-face 28B is bowl shaped.

Figure 6D:
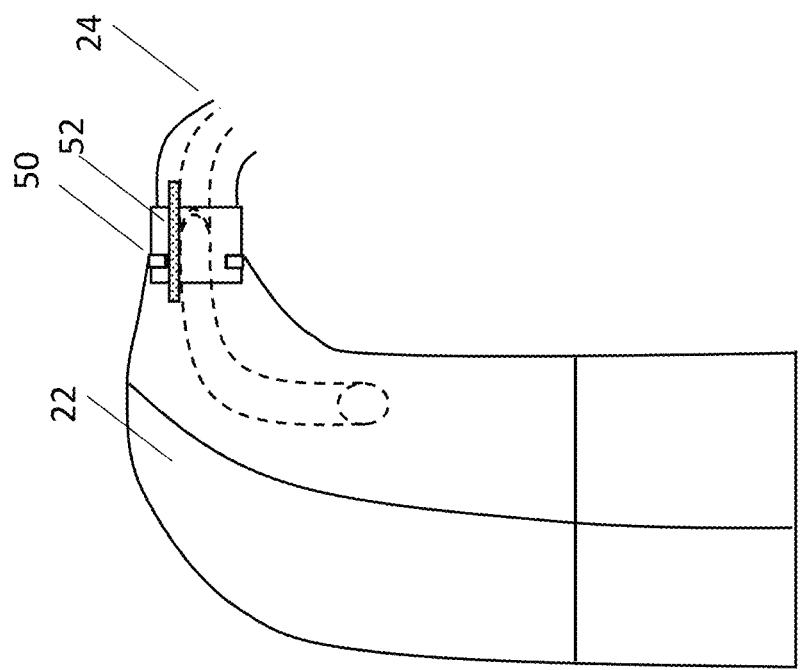
Figure 6C:
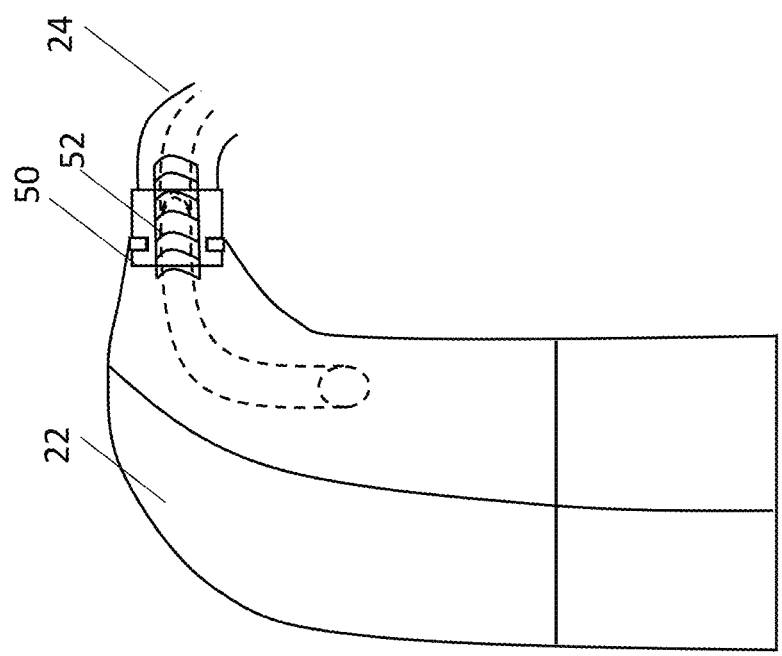

FIG. 6C illustrates a similar example of the flexible unit 50 as illustrated in FIG. 6B, however, a spring unit 52 is applied along a length of the loop structures (8A, 8B) in FIG. 6C. In this specific example, the spring unit 52 is applied along the length and at the end-faces (26B, 28B). The purpose of the spring unit 52 is to make sure that the first and the second end-faces (26, 28) are optimal arranged relative to the second inductive coil arrangement 16 when the external unit 2 is arranged onto the ear 20 and the implantable unit 14 is arranged below the skin of the user. For example, when the user wants to apply the external unit 2 onto the ear 20, the user has to move the earhook 14 into a position which allows the opening 12 to receive a part of the ear 20, and when the user releases the earhook, the earhook will return back such that an optimal inductive connection between the first and the second inductive coil arrangement (6, 16) is obtained.

The spring unit 52 may have one stable equilibrium position.

FIG. 6D illustrates another example of the spring unit 52. In this example, the spring unit 52 is a metal spring which is shaped for obtaining two stable equilibrium positions of the earhook 24 relative to the housing 22. The spring unit 52 is within the flexible unit 50 and separated from the loop structure 8.

Alternative, the flexible unit 50 may be formed as a sleeve which is configured to receive the housing 22 at one end and at the other end the earhook 24. The housing 22 and the earhook 24 is snap coupled to the flexible unit 50 preventing the flexible unit 50 to be accidently released from the housing 22 and the flexible unit 24. The earhook 24 is configured to rotate in a direction around the centre of a hollow section of the flexible unit 50.

Figure 7:
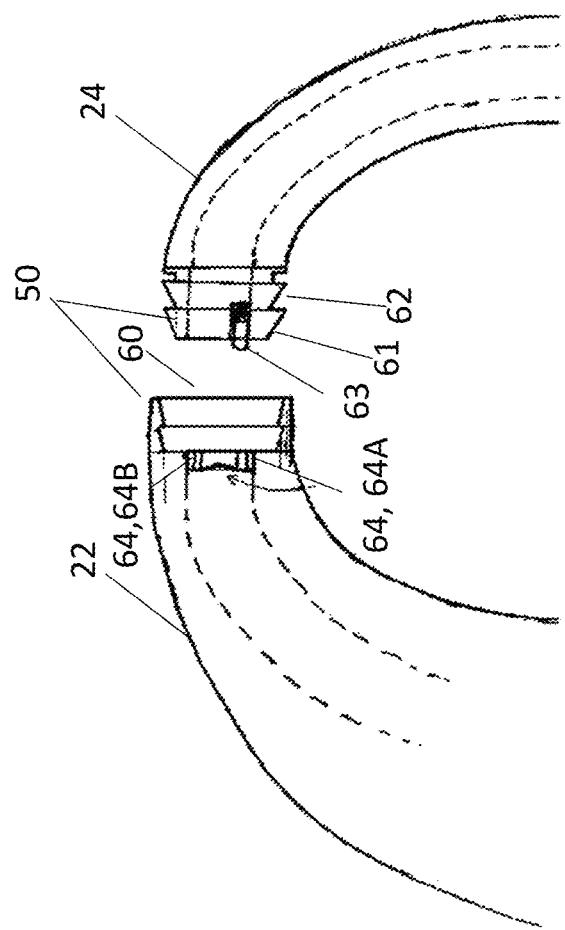
FIG. 7 illustrates an example of the flexible unit.

FIG. 7 illustrates an example of the flexible unit 50. An inner side of an opening 60 of the housing 22 includes protrusions which is configured to receive and seal the earhook 24. The end 61 of the earhook which is configured to be inserted into the opening 60 includes an inner side which has protrusions configured to couple with the protrusions of the opening 60 while inserting the end 61 of the earhook 24 into the opening 60 of the housing, and thereby, the housing 22 is sealable connected to the earhook 24. The earhook is rotatable around a centre of the opening 60. The flexible unit 50 includes a pin 63 configured to rotate freely within a trace 64 of the flexible unit 50 and between a first fixed position 64A and a second fixed position 64B. When rotating the earhook 24, the pin 63 moves within the trace 64, and when the pin 63 reaches either the first or the second fixed position 64B, the earhook 24 is fixed into a position which allows the user to take off the earhook 24 from the ear 20 or which allows optimal inductive coupling between the first and the second inductive coil arrangement (6, 16).

FIG. 8 illustrates an example of the external unit 2 where the end-face 61 of the earhook 24 and a circumferential edge of the opening 60 are shaped for preventing the user to assemble the earhook 24 with the housing 22 wrongly. In this specific example, the end-face 61 of the earhook 24 and the circumferential edge of the opening 60 are step formed (71, 72), and an inward part 75 of the opening 60 is configured to receive an outward part 73 of the end-face 61, and an outward part 76 of the opening 60 is configured to receive an inward part 74 of the end-face while the another end-faces (26B, 28B) snap couples 74. No snap coupling between the another end-faces (26B, 28B) will appear, if for example, the outward parts meets when trying to assemble the earhook 24 and the housing 22.

Figure 9A:
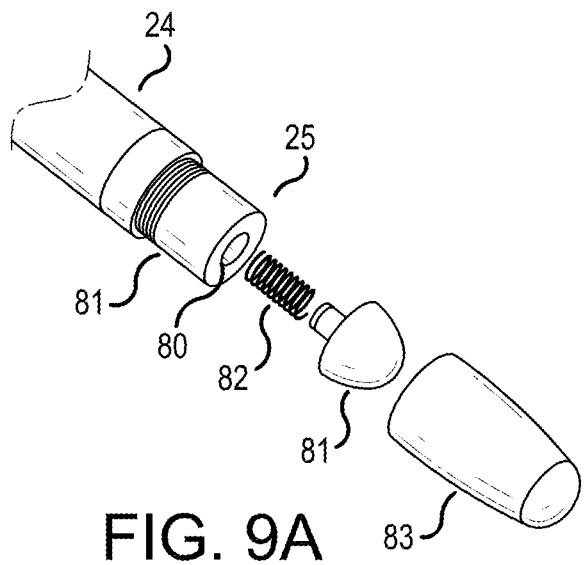
FIGS. 9A to 9D illustrate different examples of a tip of an earhook.
Figure 9B:
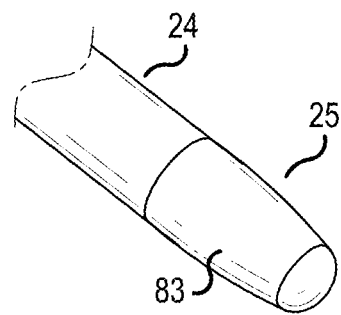

FIGS. 9A to 9D illustrate different examples of the tip 25 of the earhook 24. FIGS. 9A and 9B illustrate an example of the tip 25 which includes a first part 81 mounted into the earhook 24 and which may comprise the first end-face 26 of the loop structure 8. The first part has a hollow spring section 80 which is configured to receive a spring 82 and a tip part 81. A second part 83 is configured to be assembled to the first part 81 such that the spring 82 and the tip part 81 are kept in place within the tip 25. When the tip part 81 touches the skin of the ear the spring force of the spring 82 is configured to reduce the clamping force between the ear and the opening 12 of the external unit 2. Thereby, the external unit 2 is adaptable to different ear thicknesses.

Figure 9C:
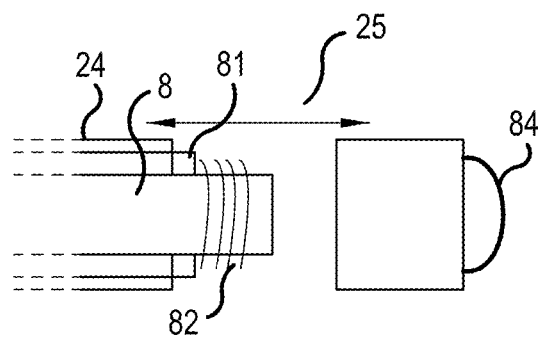
Figure 9D:
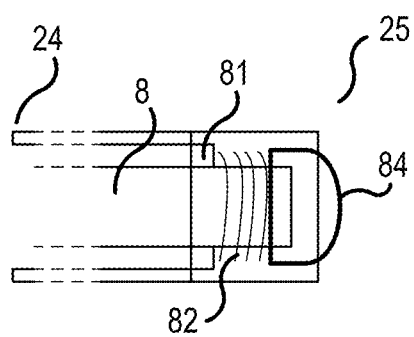

FIGS. 9C and 9D illustrate yet another example of the tip 25. The first part 81 is mounted into the earhook 24, and the first part 81 includes the first end-face 26 of the loop structure 8. The tip 25 includes a spring 82 wounded around the first end-face 26 of the loop structure 8. The tip 25 includes a tip part 84 which comprises a hollow section configured to receive the spring 82 and a part of the first end-face 26 when assemble the tip part 84 onto the first part 81. Thereby, the external unit 2 is adaptable to different ear thicknesses and the distance between the first end-face and the second end-face is reduced.

Figure 10B:
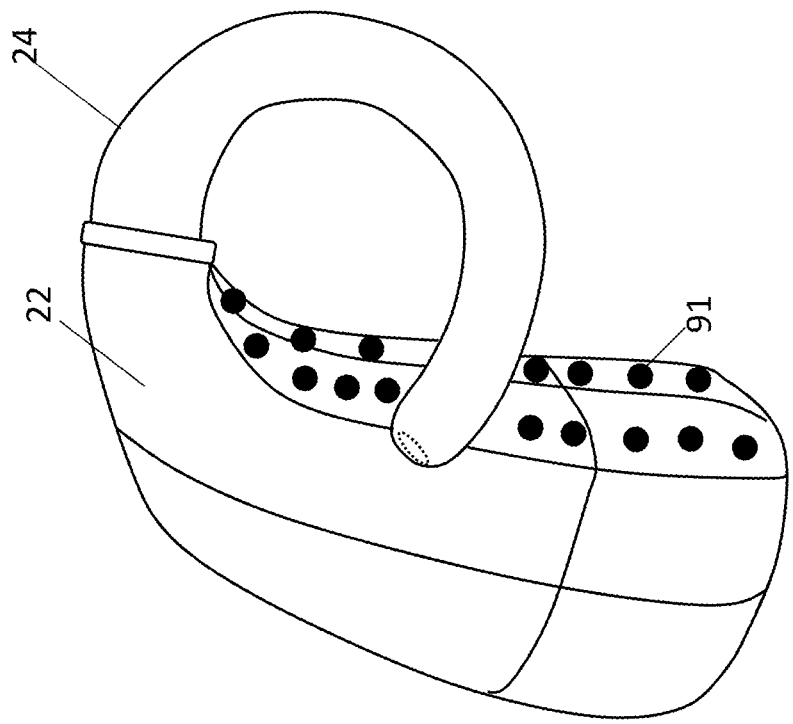
FIGS. 10A and 10B illustrate different examples of the housing.
Figure 10A:
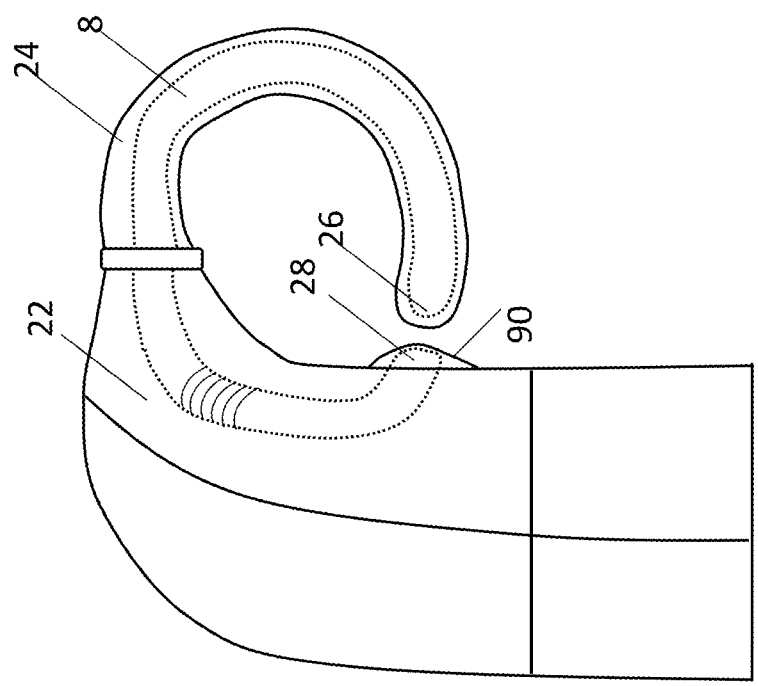

FIGS. 10A and 10B illustrate different examples of the housing 22 of the external unit 2. In FIG. 10A, an outer surface 23 of the housing 22 includes an outward pocket 90. When the user applies the external unit 2 onto the ear 20, and when the external unit 2 is in an optimal position for obtaining the optimal coupling between the coil arrangements (6, 16), the outward pocket 90 is partially or fully inserted into the hollow section 30 from one side of the second inductive coil arrangement 16 while the tip 25 of the earhook is partially or fully inserted into the hollow section 30 from an opposite side to the one side of the second inductive coil arrangement 16. A tactile signal is generated between the outward pocket 90 and the hollow section 30 of the second inductive coil arrangement 16 when the outward pocket 90 is partially or fully inserted into the hollow section 30. The purpose of the tactile signal is to make the user aware of that the external unit 2 is in the optimal position.

In FIG. 10B, an outer surface of the housing which is directed towards the skin of the ear when the external unit 2 is arranged onto the ear includes multiple protrusions 91 for the purpose of reducing possible skin irritation. For example, the skin irritation may be due to heat generation between the housing and the skin of the ear, and by applying the protrusions 91 onto the surface 23, air is able to travel through the spaces between the protrusions while the external unit 2 is on the ear 20. The air cools the part of the ear which is in contact with the protrusions 91.

Figure 11:
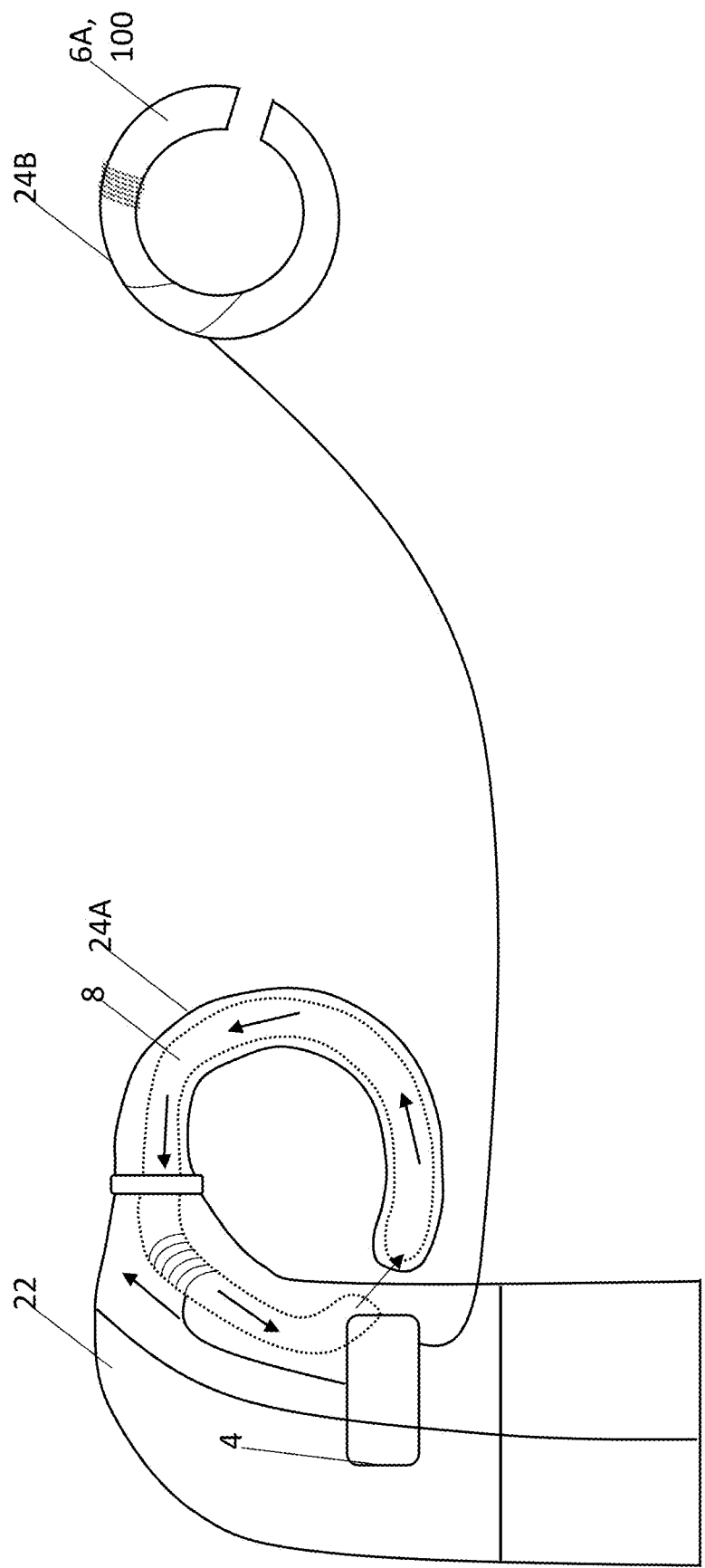
FIG. 11 illustrates an implantable hearing aid system.

FIG. 11 illustrates an implantable hearing aid system which includes at least another earhook 24B including a first secondary inductive coil arrangement 6A, and wherein the electronic unit 4 is configured to be connected to the first inductive coil arrangement 6 and the first secondary inductive coil arrangement 6A. In this example, the implantable unit 14 includes at least a second secondary inductive coil arrangement (not shown) configured to form another transcutaneous link (not shown) with a loop structure 100 of the first secondary inductive coil arrangement 6A and to receive power and/or data signals over the another transcutaneous link from the first secondary inductive coil arrangement 6A, and where the second secondary inductive coil arrangement is configured to be implanted fully or partially within a part of the ear of the user.

The second secondary inductive coil arrangement may be arranged within the opposite ear of the ear where the second inductive coil arrangement is arranged. Thereby, a binaural implantable hearing aid system is provided.

The second secondary inductive coil arrangement may be arranged within the same ear as where the second inductive coil arrangement is arranged. Thereby, the amount of power and/or data signals to be transferred in the transcutaneous link is increased without increasing the delay between the signals.

The implantable unit includes at least a second secondary inductive coil arrangement (not shown) configured to form another transcutaneous link with a loop structure of the first secondary inductive coil arrangement and to receive power and/or data signals over the another transcutaneous link from the first secondary inductive coil arrangement, and where the second secondary inductive coil arrangement is configured to be implanted fully or partially within a part of the ear of the user.

Figure 12A:
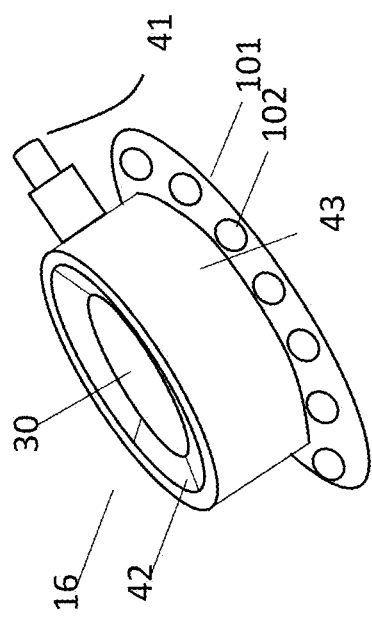
FIGS. 12A and 12B illustrate an example of the second inductive coil arrangement.
Figure 12B:
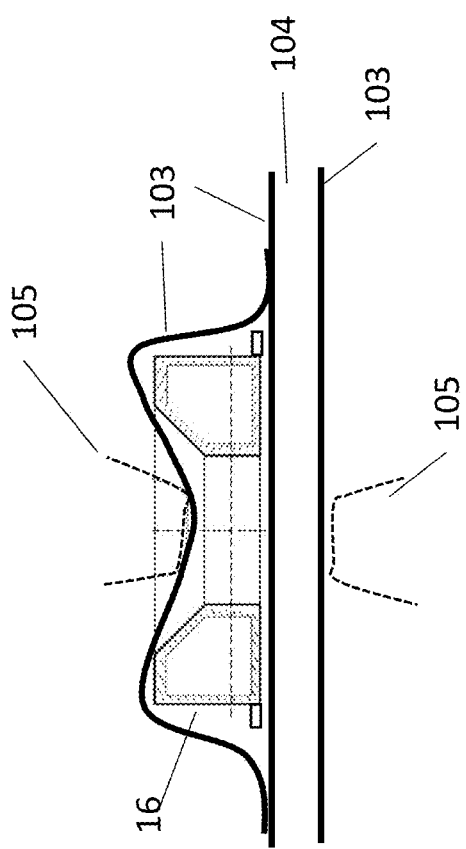

FIGS. 12A and 12B illustrate an example of the second inductive coil arrangement 16 with a flange 101 which includes multiple holes for improving tissue anchoring of the coil arrangement 16. The multiple holes may be ingrowth means for skin and/or tissue to grow into, and thereby, the second inductive coil arrangement 16 is anchored within the ear. In FIG. 12B, the implantable unit 14 is in place and the second inductive coil arrangement 16 is arranged between the skin layer 103 and the cartilage layer 104 of the ear 20. After the implantation of the implantable unit 14 a healing clip 105 is mounted onto the ear and the coil arrangement 16 for keeping the coil arrangement 16 in place during interdigitation of tissue around the coil arrangement 16. The healing clip 105 improves the healing process of the ear after the implantation and the anchoring of the coil arrangement 16 within the ear.

Figure 13C:
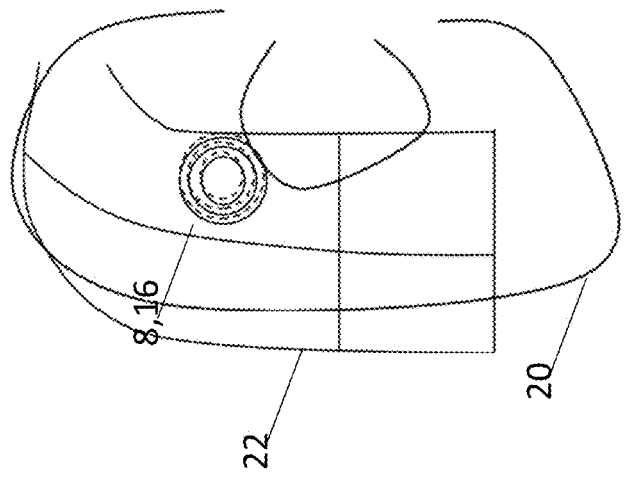
FIGS. 13A to 13C illustrate examples of loop structure and second indicative coil arrangements.
Figure 13B:
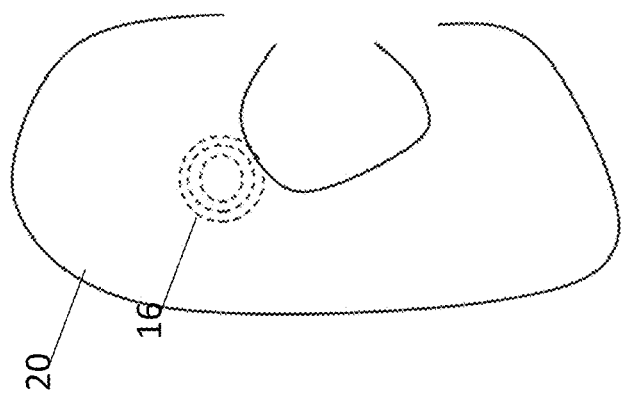
Figure 13A:
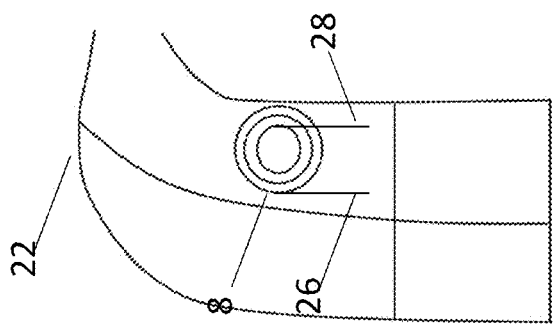

FIG. 13A illustrates an example where the first end-face 26 and the second end-face 28 of the loop structure 8 is arranged within the housing 22, and where the loop structure 8 includes multiple loops. FIG. 13B illustrates an example where the second inductive coil arrangement 16 implanted in the ear, for example, in the antihelix region of the ear. In this specific example, the second inductive coil arrangement 16 includes multiple loops. FIG. 13C illustrates an example where the housing 22 is a behind-the-ear hearing aid arranged behind the ear, and where the multiple loops of the loop structure 8 is aligned with the multiple loops of the second inductive coil arrangement. The alignment of the loop structure 8 and the second inductive coil arrangement 16 implies that the multiple loops of both loop structure 8 and the coil arrangement 16 are parallel or about parallel.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. An implantable hearing aid system comprising:
    an external unit including an electronic unit operationally coupled to a first inductive coil arrangement configured to transmit power and/or data signals, and where the first inductive coil arrangement includes a loop structure with coils wound around and along at least a part of length of the loop structure, and the loop structure comprises an opening,
    an implantable unit including a second inductive coil arrangement configured to form a transcutaneous link with the loop structure and to receive the power and/or data signals over the transcutaneous link, and where the second inductive coil arrangement is configured to be implanted fully or partially within a part of an ear of a user of the implantable hearing aid system, and wherein the external unit includes a housing and an earhook, and where a first end-face of the loop structure is arranged within the earhook and a second end-face of the loop structure is arranged within the housing, and
    wherein, when the external unit is worn by the user, the first end-face is configured to face the second end-face, thereby forming the loop structure, and wherein skin of the ear of the user is located between the first end-face and the second end-face.

2. The implantable hearing aid system according to claim 1, comprising a flexible unit, wherein the earhook is connected to the housing of the external unit by the flexible unit, and where the earhook is configured to be in a first position and at least a second position when applying a force onto the earhook.

3. The implantable hearing aid system according to claim 2, wherein the flexible unit includes a rotating mean which is configured to rotate the earhook or at least a part of the earhook between the first position and at least the second position.

4. The implantable hearing aid system according to claim 2, wherein the size of the opening of the loop structure can be adjusted in terms of changing the position of the earhook between the first position and at least the second position.

5. The implantable hearing aid system according to claim 3, wherein the size of the opening of the loop structure can be adjusted in terms of changing the position of the earhook between the first position and at least the second position.

6. The implantable hearing aid system according to claim 1, wherein the earhook is connected to the housing by a connector part, wherein the connector part includes one or more wires connecting the loop structure with the electronic unit.

7. The implantable hearing aid system according to claim 1, wherein the earhook comprises a tip with a compression reducing mean, and wherein the tip is configured to touch the skin of the part of the ear when the external unit is worn by the user.

8. The implantable hearing aid system according to claim 7, wherein the compression reducing mean includes a spring configured to be compressed when the tip is touching the skin.

9. The implantable hearing aid system according to claim 7, wherein the compression reducing mean is made of a foam material.

10. The implantable hearing aid system according to claim 1, wherein at least a part of the second inductive coil arrangement is arranged in at least one of the following parts of the ear: helix, antihelix, scapha, triangular fossa, pinna, auricular lobule(earlobe), and concha.

11. The implantable hearing aid system according to claim 1, wherein the opening is arranged between the first end-face and the second end-face of the loop structure, and wherein the two end-faces are directed fully or partially towards each other at one position of the earhook.

12. The implantable hearing aid system according to claim 1, wherein a winding density of the coils along the loop structure of the first inductive coil arrangement is higher in the vicinity of the first end-face and the second end-face of the loop structure as compared to the remaining parts of the loop structure.

13. The implantable hearing aid system according to claim 1, wherein the second inductive coil arrangement includes an implantable housing which comprises an implantable loop structure with coils wound around and along at least a part of length of the implantable loop structure, and wherein the implantable housing includes a through-going hole, and the through-going hole is configured to have an overlapping interface with the first inductive coil arrangement.

14. The implantable hearing aid system according to claim 13, wherein the through-going hole of the implantable housing has an inner side which is chamfered.

15. The implantable hearing aid system according to claim 13, and wherein at least a part of the first inductive coil arrangement is arranged within or vicinity to the through-going hole of the second inductive coil arrangement when the external unit is worn at the ear of the user.

16. The implantable hearing aid system according to claim 1, wherein at least a tip of the earhook or an end-face of the loop structure of the first inductive coil arrangement is configured to have an overlapping interface with the second inductive coil arrangement.

17. The implantable hearing aid system according to claim 1, wherein the external unit includes a shielding unit configured to magnetically shield the electronic unit and other units of the external unit from unwanted external electromagnetic fields provided by the first inductive coil arrangement.

18. The implantable hearing aid system according to claim 1, comprising at least another earhook including a first secondary inductive coil arrangement, and wherein the electronic unit is configured to be connected to the first inductive coil arrangement and the first secondary inductive coil arrangement.

19. The implantable hearing aid system according to claim 18, wherein the implantable unit includes at least a second secondary inductive coil arrangement configured to form another transcutaneous link with a loop structure of the first secondary inductive coil arrangement and to receive power and/or data signals over the another transcutaneous link from the first secondary inductive coil arrangement, and where the second secondary inductive coil arrangement is configured to be implanted fully or partially within a part of the ear of the user.

20. The implantable hearing aid system according to claim 1, wherein the external unit is a behind-the-ear hearing aid, an in-the-ear hearing aid, or an earhook hearing aid.

* * * * *